United States Patent
Rueger et al.

(10) Patent No.: US 7,312,857 B2
(45) Date of Patent: *Dec. 25, 2007

(54) METHOD AND SYSTEM FOR MONITORING PLASMA USING OPTICAL EMISSION SPECTROMETRY

(75) Inventors: Neal R. Rueger, Boise, ID (US); Kevin T. Hamer, Meridian, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/219,540

(22) Filed: Sep. 1, 2005

(65) Prior Publication Data

US 2006/0007425 A1   Jan. 12, 2006

Related U.S. Application Data

(63) Continuation of application No. 10/682,017, filed on Oct. 9, 2003, now Pat. No. 6,950,178.

(51) Int. Cl.
*G01J 3/30* (2006.01)

(52) U.S. Cl. .................................. 356/72; 356/316
(58) Field of Classification Search .............. 356/72, 356/316

See application file for complete search history.

(56) References Cited

U.S. PATENT DOCUMENTS

| 5,910,011 A | 6/1999 | Cruse ........................... 438/16 |
| 6,818,561 B1 | 11/2004 | Sonderman ................. 438/706 |
| 7,072,028 B2 * | 7/2006 | Powell et al. .................. 356/72 |
| 2003/0226970 A1 * | 12/2003 | Yatsiv ......................... 356/311 |
| 2005/0046825 A1 * | 3/2005 | Powell et al. .................. 356/72 |

\* cited by examiner

Primary Examiner—Gregory J. Toatley, Jr.
Assistant Examiner—Kara E Geisel
(74) Attorney, Agent, or Firm—Fletcher Yoder

(57) ABSTRACT

A method and system are presented for monitoring the optical emissions associated with a plasma used in integrated circuit fabrication. The optical emissions may be processed by an optical spectrometer to obtain a spectrum. The spectrum may be analyzed to determine the presence of particular disassociated species which are indicative of the presence of a suitable plasma and which may be desired for a deposition, etching, or cleaning process.

18 Claims, 2 Drawing Sheets

METHOD AND SYSTEM FOR MONITORING PLASMA USING OPTICAL EMISSION SPECTROMETRY

CROSS-REFERENCE TO RELATED APPLICATION

This application is a continuation of U.S. patent application Ser. No. 10/682,017 by Neal R. Rueger and Kevin Hamer, entitled "Method and System for Monitoring Plasma Using Optical Emission Spectrometry," filed on Oct. 9, 2003 now U.S. Pat. No. 6,950,178, incorporated herein by reference.

BACKGROUND OF THE INVENTION

1. Field of the Invention

This present invention relates generally to the field of integrated circuit manufacturing and, more specifically, to the monitoring of plasma used in the manufacture of integrated circuits.

2. Description of the Related Art

This section is intended to introduce the reader to aspects of the art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the manufacturing of integrated circuits, numerous microelectronic circuits may be simultaneously manufactured on a semiconductor substrate. These substrates are usually referred to as wafers. A typical wafer is comprised of a number of different regions, known as die regions. When fabrication is complete, the wafer is cut along these die regions to form individual die. Each die contains at least one microelectronic circuit, which is typically replicated on each die. One example of a microelectronic circuit which can be fabricated in this way is a dynamic random access memory.

Although referred to as semiconductor devices, integrated circuits are in fact fabricated from numerous materials of varying electrical properties. These materials include insulators or dielectrics, such as silicon dioxide, and conductors, such as aluminum, tungsten, copper, and titanium in addition to semiconductors, such as silicon and germanium arsenide. By utilizing these various materials, the various transistors, gates, diodes, vias, resistors, and connective paths comprising the integrated circuit may be formed. Because of the complexity, both in materials and in design, incorporated into integrated circuits, the integrated circuit can be designed to perform a variety of functions within a limited space.

In manufacturing these complex integrated circuits, plasmas may be generated and used to facilitate different aspects of the process. For example, plasmas may be used to facilitate the deposition of one or more of the layers comprising the integrated circuit. In particular, plasma enhanced chemical vapor deposition (PECVD) may be used to deposit layers or films of silicon nitride ($SiN_x$), silicon dioxide ($SiO_x$), silicon oxide nitride ($SiO_xN_x$), as well as metals, such as titanium, and metal-containing films, such as titanium nitride (TiN). In addition, plasmas may be used to facilitate the etching of fine structures in a layer of material on a substrate.

In addition to depositing the desired materials as layers on the substrate, the deposition process may result in layers of material being deposited on the exposed surfaces of the deposition chamber. If left to accumulate, the materials deposited on the surfaces of the chamber may eventually chip or "spall" off as particles or flakes which can contaminate future deposition processes. Therefore, a plasma may also be used to clean or etch the chamber surfaces periodically to prevent accumulations of the deposited materials on the chamber surfaces.

The plasma itself is a partially ionized gas comprising highly reactive radicals and ions. The highly reactive radicals and ions comprise the reactive species needed to perform the desired deposition, etching, or cleaning processes and are typically generated from the disassociation of precursor molecules. Examples of precursor molecules include, but are not limited to, silane ($SiH_4$), germane ($GeH_4$), ammonia ($NH_3$), phosphine ($PH_3$), nitrogen trifluoride ($NF_3$), titanium chloride ($TiCl_4$), tantalum chloride ($TaCl_5$), molybdenum hexafluoride ($MoF_6$), tetraethyl orthosilicate (TEOS) ($Si(OC_2H_5)_4$) and tungsten fluoride ($WF_6$).

In a deposition context, the reactive radicals and/or ions generated from the disassociation of the precursor may interact with a substrate surface, such as a wafer, to from a layer of solid material on the surface. For example, silane or tetraethyl orthosilicate are precursors which, in conjunction with oxygen, may be used to deposit silicon dioxide on a substrate. By contrast, in an etching or cleaning context, the reactive radicals and/or ions generated from the disassociation of the precursor may interact with deposited material to break down the deposited material into various gaseous byproducts which may then be flushed from the reactor. For example, nitrogen trifluoride is a precursor which, upon disassociation, is effective at etching or removing silicon dioxide.

The plasma to be used in these processes may be generated by various means. For example, a plasma may be generated by applying sufficient voltage, typically an AC or RF voltage, between two electrodes. Alternately, microwaves may be used to generate the plasma by heating the electrons of the precursor, thereby inducing atomic collisions which lead to precursor disassociation and plasma formation. A magnetron may be used to generate the microwave energy used to produce the plasma.

The successful generation of the plasma during the processes discussed above may be determined by an optical detector positioned in a viewport or window of the applicator. In particular, the optical detector may measure light emission within the reactor and, based on some threshold, may thereby determine if a plasma has been formed. However, in some instances, it has been found that the detector threshold may be exceeded, thereby indicating the presence of a plasma, when the plasma is insufficient or inadequate for the desired task. For example, a precursor may be sufficiently disassociated to register as a plasma, but insufficiently disassociated to actually perform the desired function, such as deposition, etching, or cleaning. Such an unsuitable plasma may arise due to magnetron tube age, deterioration in a microwave-based system, or electrode fouling in a RF or voltage system.

Regardless of the cause of the plasma deficiency, however, the failure of the optical detector to warn of an unsuitable plasma may lead to wasted time and/or resources if the failure of the plasma facilitated processes is not otherwise recognized. In particular, the optical detector may fail to detect the unsuitability of the plasma for an indefinite period before the plasma quantity or quality deteriorates below the configured threshold to generate an error or warning message. It is therefore desirable to determine more accurately when a plasma is unsuitable to facilitate a desired process, such as a deposition, etching, or cleaning process, and thereby to minimize the problems arising due to the plasma deficiency.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Integrated circuitry, in one form or another, is present in substantially all consumer, commercial, and industrial electronic devices. For example, microprocessors, memory circuits, control circuits, video processors, and so forth, are examples of integrated circuits which may be present in display devices, such as televisions, monitors, computers, pagers, cellular telephones, personal digital assistants, entertainment systems, gaming consoles, motor vehicles, inventory tracking systems, registers, medical diagnostic equipment, and so forth. The integrated circuits themselves typically comprise one or more semiconductor devices that provide the functionality of the integrated circuit.

The semiconductor devices are typically dies fabricated by applying assorted deposition and etching processes to a silicon wafer substrate. The proper functioning of the semiconductor device, therefore, typically depends upon the integrity and purity of the layers comprising the device. Consequently, inadvertent contamination during deposition, incomplete etching, and/or incomplete deposition of one or more of the deposited layers may lead to defective semiconductor devices and to reduced yields from the fabrication process.

In the case of contamination, failure of the periodic cleaning process may allow a residue composed of the deposition material or materials to build up on the exposed surfaces of the deposition chamber. The deposition residue may eventually spall off as chips, flakes, or particles in response to the mechanical stresses generated by thermal cycling within the chamber and the continued accretion of the residue. The chips, flakes, or particles may contaminate layers or films subsequently deposited on wafer substrates within the uncleaned deposition chamber, causing defects in the circuit patterns on wafers processed in the chamber.

Figure 1:
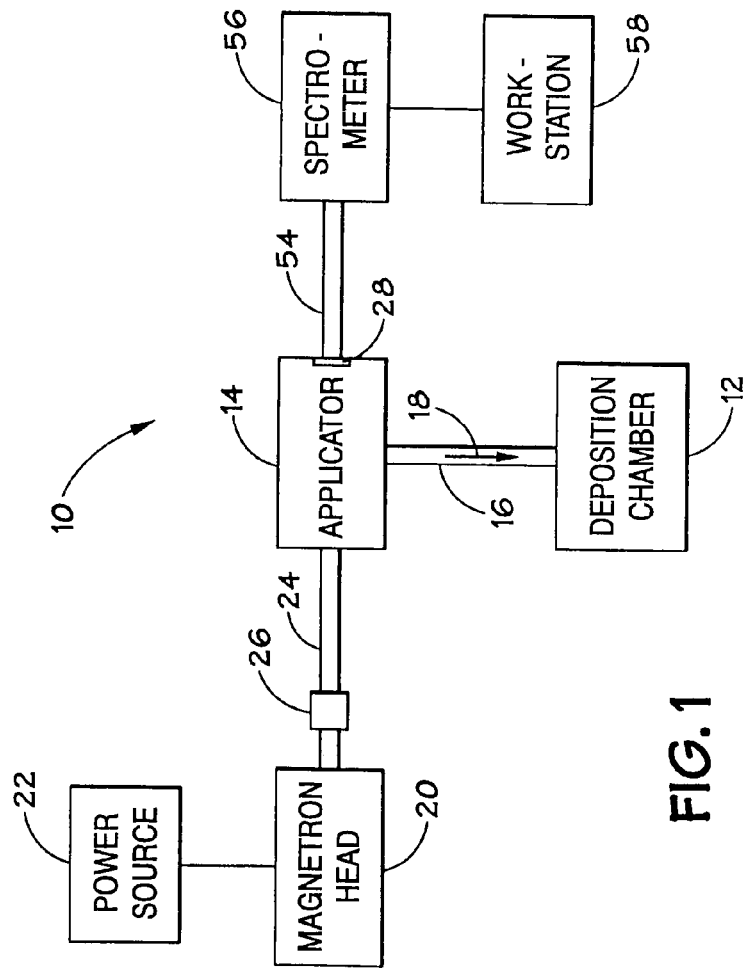
FIG. 1 illustrates an exemplary remote plasma cleaning subsystem in accordance with the present technique.

For example, high density plasma chemical vapor deposition (HDP-CVD) may be used to deposit dielectric thin films, such as silicon dioxide ($SiO_2$) and/or silicon nitride ($Si_3N_4$), on a wafer substrate situated in a deposition chamber. In addition to being deposited on the wafer substrate, the $SiO_2$, $Si_3N_4$, and/or other dielectric material may be deposited on the exposed surfaces of the deposition chamber. The residual materials deposited on the deposition chamber surfaces may be removed by a remote plasma cleaning subsystem 10, as depicted in FIG. 1, thereby preventing or minimizing contamination by particles of the residue material.

The remote plasma cleaning system 10 provides periodic in situ cleaning of the deposition chamber 12 using disassociated nitrogen trifluoride ($NF_3$). The $NF_3$ is disassociated by a plasma into charged and neutral species, including N, F, and $NF_x$, in an applicator 14 that is composed of a dielectric material, such as sapphire or ceramic. The applicator 14 is connected to the deposition chamber 12 by a transport tube 16 that allows gaseous particles to travel from the applicator 14 to the deposition chamber 12. Because the plasma is generated and maintained in the applicator 14 and because ions, i.e., charged species, quickly react to form neutral byproducts, primarily neutral species traverse the transport tube 16 to reach the deposition chamber 12. These neutral species include fluorine radicals 18, i.e., atomic fluorine, which react with residual $SiO_2$ and/or $Si_3N_4$ to form gaseous silicon tetrafluoride ($SiF_4$), hydrogen fluoride (HF), fluorine ($F_2$), nitrogen ($N_2$), and oxygen ($O_2$), which may be flushed from the deposition chamber 12. Because the plasma is generated and maintained in the applicator 14 and the cleaning process occurs in the deposition chamber 12, the process is known as a remote plasma cleaning processing.

The high density plasma is generated and maintained in the applicator 14 by the application of microwave energy within the applicator 14. The microwave energy may be generated by a magnetron head 20 powered by a power source 22. A waveguide 24 directs the microwave energy from the magnetron 20 to the applicator 14. A circulator/isolator 26 protects the magnetron head 20 from reflected power during plasma ignition within the applicator.

Traditionally, to determine the presence of the high density plasma in the applicator 14, an optical emission detector would be employed at a viewport 28 to measure light emission. However, as discussed previously, light emission alone may not be sufficient to determine if adequate $NF_3$ disassociation has occurred. For example, a faulty magnetron tube may provide sufficient microwave energy to generate enough plasma to produce measurable light emissions, but not enough to disassociate the $NF_3$. In such a case, fault or error warning systems relying upon an optical emission detector may fail. In this manner, traditional processes based on optical emission detection alone may provide no warning that $NF_3$ disassociation is not occurring, resulting in increased contamination during die fabrication and consequently lower yields.

Figure 2:
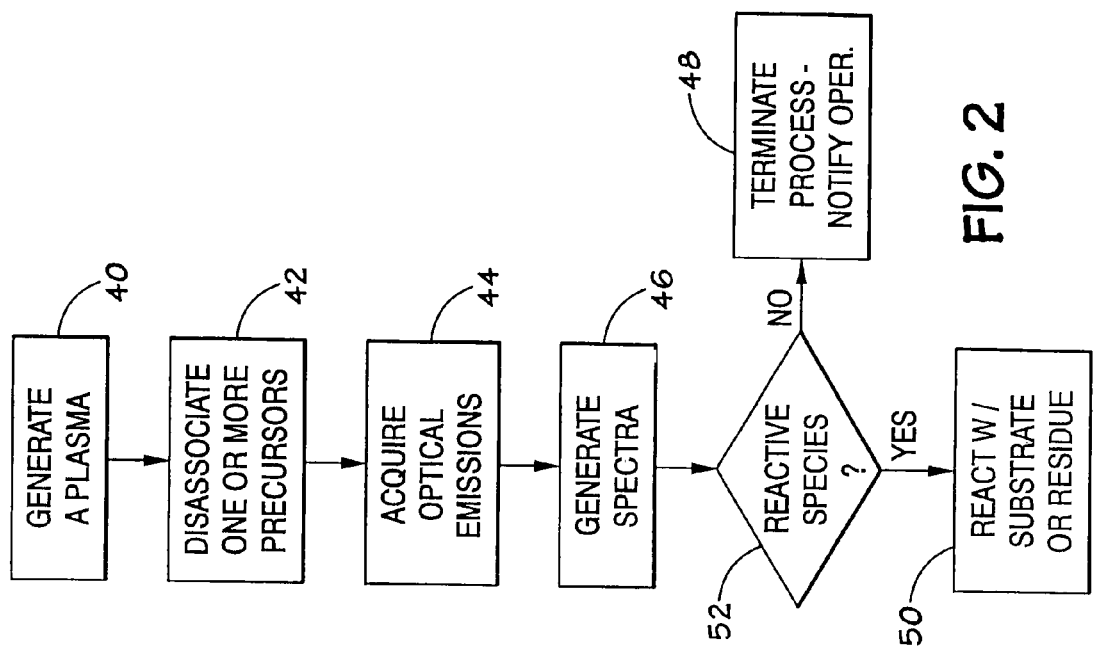
FIG. 2 illustrates a flowchart of a procedure for monitoring precursor disassociation generated in accordance with the present technique.

To address this deficiency, a spectrum, such as an optical spectrum, may be generated from emissions associated with the plasma and/or precursor to determine if precursor disassociation has occurred. For example, referring to FIG. 2, plasma may be generated in a plasma chamber, such as in the applicator 14, as depicted by the plasma generation block 40. The plasma is then used to disassociate one or more precursors, as depicted by the disassociation block 42. As depicted by the acquisition block 44, emissions, such as optical emissions, are acquired from the plasma chamber. One or more spectra may then be generated from the emissions, such as by an optical spectrometer, as depicted at the spectrum generation block 46. Based upon the one or more spectra, the plasma-based process is either terminated and an operator notified of an error condition, as depicted by termination block 48, or the process is allowed to proceed, as depicted by reaction block 50.

The decision to terminate or proceed, as depicted by the decision block 52, may be based upon the characteristics of a spectrum or spectra generated in this manner. The decision may be based upon whether all or part of the spectrum or spectra coincide, within certain tolerances, with an expected or reference spectrum. In particular, characteristic signatures, such as peaks indicating the presence of reactive species, may be measured and/or compared. For example, the amplitude of a peak corresponding to fluorine radicals 18 may be measured and, if outside a desired tolerance, such as a 5% or 10% deviation, the decision may be made to proceed to terminate the process or notify the operator, as depicted at termination block 48. Conversely, the amplitude of a fluorine radical peak within the desired tolerance may indicate that disassociation of the precursor has occurred in the plasma chamber and, therefore, that a suitable plasma has been generated by generation block 40. The process may therefore be allowed to proceed, as depicted by reaction block 50.

While the present technique may be useful in determining the efficacy of plasma generation in a remote plasma cleaning system, it is equally applicable to remote etching or deposition processes. Furthermore, to the extent that the emissions are detectable in a deposition chamber, either via a probe or a viewport 28 transparent to the desired wavelengths, the present technique may also be employed in direct plasma processes, i.e. processes in which the plasma is generated in the same chamber as the deposition, etching, or cleaning event occurs. Any suitable form of spectroscopy, such as optical, near infrared, or Raman, may be employed provided that suitable emissions are obtainable and the reactive species to be detected generate a characteristic signature in the generated spectra.

For example, returning to FIG. 1, a fiber optic cable 54 or other emission conductive medium may be mounted to the viewport 28. Optical emissions from the applicator 14 may then be directed to an optical spectrometer 56 via the optical cable 54. Within the optical spectrometer 56, the optical emission may be run through a diffraction grating to split the light into an interference pattern or otherwise analyzed to generate optical spectra, such as the spectra depicted in FIG. 3. The optical spectra obtained from the optical spectrometer 56 may be used, as described above, to determine a failure condition in the cleaning and/or etching process associated with the plasma generation and/or the disassociation of $NF_3$.

Figure 3:
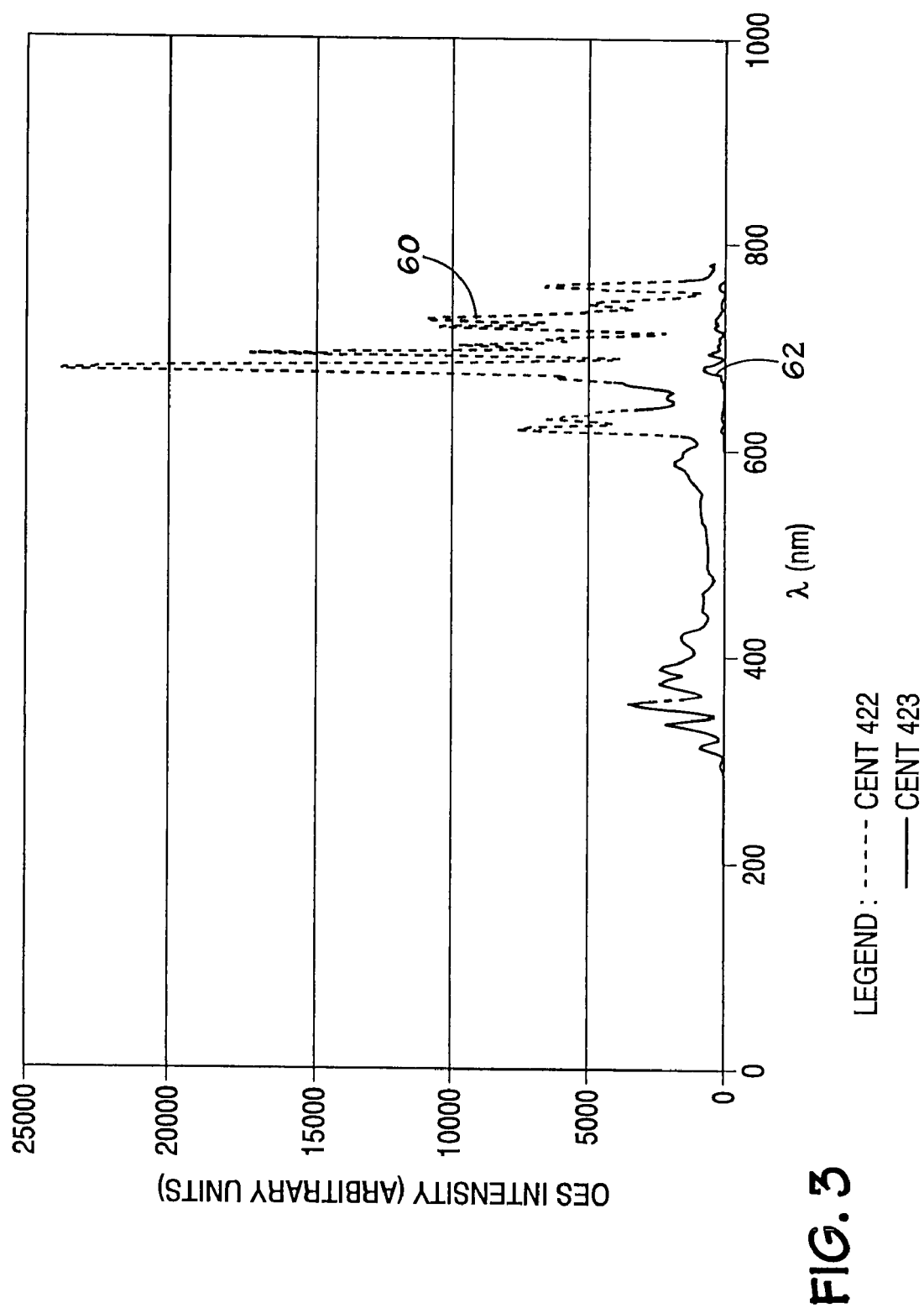
FIG. 3 illustrates optical emission spectra of disassociated and associated $NF_3$ in accordance with the present technique.

Examples of spectra which may be obtained by the present techniques are depicted in FIG. 3. For example, the first spectrum 60 is generated from optical emissions acquired from an applicator 14 in which a suitable plasma is generated and $NF_3$ disassociation has occurred. The vertical axis of the spectrum 60 is intensity, which may be an arbitrary unit, such as incidence or data counts, while the horizontal axis is wavelength, $\lambda$, measured in nm. In the first spectrum 60, $N_2$ and $N_2^+$ peaks are present between approximately 300 nm-525 nm and comprise a characteristic signature, as discussed above.

The second spectrum 62, however, is generated from optical emissions measured from an applicator 14 in which a suitable plasma was not generated and $NF_3$ disassociation has not occurred. Therefore, as one might expect, the signature associated with $N_2$ and $N_2^+$ is absent. Furthermore, the optical emission intensity of the second spectrum 62 is one-third that of the first spectrum 60. Though the second spectrum 62 is clearly indicative of a disassociation failure, the light emissions alone, as might be acquired by an optical detector mounted at the viewport 28, may fail to indicate the fault condition. In particular, the optical detector may simply indicate the presence of plasma, without indicating the sufficiency of that plasma with regard to precursor disassociation.

The spectra obtained by the spectrometer, such as first spectrum 60 and second spectrum 62 may be displayed at the spectrometer 56 or on workstation 58 or other processor-based system in communication with the spectrometer 56. An operator may, in turn, analyze the measured spectrum or compare the measured spectrum to a reference spectrum to determine whether suitable disassociation is occurring in the applicator 14. Alternatively, routines executed on the spectrometer 56 or workstation 58 may be used to compare the intensity of the measured spectrum at one or more wavelengths of interest to the reference or expected intensities within a configured tolerance. For example, the spectrum or spectra may be read by an array of photosensitive elements, such as photodiodes, such that each photodiode corresponds to a wavelength or a wavelength increment. The output of the one or more photodiodes corresponding to the wavelength or wavelengths of interest may be converted, as necessary, into a computer readable format, such as by an analog-to-digital converter. The comparison routines may then compare the photodiode output at the desired wavelengths with the reference or expected output, in accordance with the techniques described herein. Based on the comparison, the computer executed routine may take no action, may recommend an action to an operator, and/or may terminate the cleaning process pending operator action or correction.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method for determining the adequacy of a plasma, comprising:
    generating a plasma in a plasma chamber to attempt to disassociate one or more precursors in the plasma chamber to form two or more reactive species;
    acquiring optical emissions from the plasma chamber;
    generating one or more optical emission spectra from the optical emissions;
    automatically determining whether at least one reactive species is present in the plasma chamber based upon the one or more optical emission spectra;
    performing an action or no action based on the automatic determination.

2. The method as recited in claim 1, wherein the one or more precursors comprise at least one of nitrogen trifluoride, silane, germane, ammonia, phosphine, titanium chloride, tantalum chloride, molybdenum hexafluoride, tetraethyl orthosilicate, and tungsten fluoride.

3. The method as recited in claim 1, wherein acquiring optical emissions from the plasma chamber comprises automatically acquiring optical emissions from the plasma chamber.

4. The method as recited in claim 1, wherein automatically determining whether at least one reactive species is present in the plasma chamber comprises automatically comparing the intensity of the measured spectrum at one or more wavelengths of interest to a reference or an expected intensity.

5. The method as recited in claim 1, wherein the action comprises recommending an action to an operator.

6. The method as recited in claim 1, wherein the action comprises automatically terminating a process.

7. A method of remotely generating a plasma, comprising generating microwaves using a magnetron;
generating a plasma at an applicator using the microwaves;
disassociating a precursor into two or more reactive species using the plasma
receiving optical emissions from the applicator at an optical spectrometer;
generating one or more optical spectra from the optical emissions which indicate the presence or absence of the two or more reactive species; and
receiving the two or more reactive species in a deposition chamber, wherein at least one reactive species reacts with a material in the deposition chamber.

8. The method of remote plasma generation as recited in claim 7, wherein the precursor comprises at least one of nitrogen trifluoride, silane, germane, ammonia, phosphine, titanium chloride, tantalum chloride, molybdenum hexafluoride, tetraethyl orthosilicate, and tungsten fluoride.

9. The method of remote plasma generation as recited in claim 7, wherein the two or more reactive species comprise at least fluorine radicals.

10. The method of remote plasma generation as recited in claim 7, wherein the material comprises at least one of silicon dioxide or silicon nitride.

11. A method of manufacturing an integrated circuit, comprising:
situating a silicon wafer in a deposition chamber;
generating a plasma in a plasma chamber to attempt to disassociate one or more precursors in the plasma chamber to form two or more reactive species;
acquiring optical emissions from the plasma chamber;
generating one or more optical emission spectra from the optical emissions;
automatically determining whether at least one reactive species is present in the plasma chamber based upon the one or more optical emission spectra; and, if so,
processing the silicon wafer to form an integrated circuit.

12. The method as recited in claim 11, further comprising at least one of:
reacting the at least one reactive species with the silicon wafer if the at least one reactive species is determined to be present; and
terminating the production of the integrated circuit if the at least one reactive species is not determined to be present.

13. The method as recited in claim 12, wherein reacting the at least one reactive species with the silicon wafer comprises forming a deposition layer on the silicon wafer comprising a reacted form of the at least one reactive species.

14. The method as recited in claim 12, wherein reacting the at least one reactive species with the silicon wafer comprises etching an exposed layer of the silicon wafer.

15. The method as recited in claim 11, further comprising notifying an operator of an error condition if the at least one reactive species is not determined to be present.

16. The method as recited in claim 11, wherein the one or more precursors comprise at least one of nitrogen trifluoride, silane, germane, ammonia, phosphine, titanium chloride, tantalum chloride, molybdenum hexafluoride, tetraethyl orthosilicate, and tungsten fluoride.

17. The method as recited in claim 11, wherein acquiring optical emissions from the plasma chamber comprises automatically acquiring optical emissions from the plasma chamber.

18. The method as recited in claim 11, wherein automatically determining whether at least one reactive species is present in the plasma chamber comprises automatically comparing the intensity of the measured spectrum at one or more wavelengths of interest to a reference or an expected intensity.

* * * * *